United States Patent [19]

Lilaonitkul et al.

[11] 4,373,529
[45] Feb. 15, 1983

[54] TAMPON WITH WOUND PLEDGET IN THE SHAPE OF A BELL

[75] Inventors: Amnuey Lilaonitkul; Richard R. Tews, both of Appleton, Wis.

[73] Assignee: Kimberly-Clark Corporation, Neenah, Wis.

[21] Appl. No.: 262,327

[22] Filed: May 11, 1981

[51] Int. Cl.³ .................. A61F 13/20; D01G 25/00
[52] U.S. Cl. ................................... 128/285; 19/149
[58] Field of Search ............... 128/285, 270; 28/118; 19/149

[56] References Cited

U.S. PATENT DOCUMENTS

| 961,689 | 6/1910 | Dorr | 128/270 |
| 3,508,548 | 4/1970 | Hochstrasser et al. | 128/285 |
| 3,572,341 | 3/1971 | Glassman | 128/285 |

*Primary Examiner*—C. Fred Rosenbaum
*Attorney, Agent, or Firm*—Howard Olevsky; William D. Herrick

[57] ABSTRACT

This invention relates to a method for forming a wound cellulosic tampon in the shape of a truncated cone by winding a flat cellulosic web while a portion of the web which forms the outer surface of the pledget of the tampon is in contact with a tapered receptacle. The wound tampon resists telescoping during withdrawal after use.

4 Claims, 2 Drawing Figures

TAMPON WITH WOUND PLEDGET IN THE SHAPE OF A BELL

FIELD OF THE INVENTION

This invention relates to a tampon and particularly a tampon having a wound pledget.

BACKGROUND OF THE INVENTION

Recently tampons having wound pledgets have become increasingly popular, particularly in Europe. These tampons are formed from a flat absorbent web which is rolled in a jelly roll type of configuration and compressibly set with or without the presence of heat. Examples of machines currently used for the manufacture of such tampons employ a shaping receptacle which fits around the tampon pledget as the pledget is wound. The machines, however, differ in the means for winding the tampon. One of these machines is made by Karl Ruggli AG, Fisibach, Switzerland. The Ruggli machine employs a two-pronged fork which engages one end of the web. The fork is rotated while the outside of the web is in contact with the shaping receptacle to form a rolled cylindrical pledget. The other machine known as the Fulu and made by K. Fassbind-Ludwig & Co., Fulu Maschinenbau, Wugen, Switzerland utilizes a vacuum mandrel for holding one end of the web. As is the case with the Ruggli machine the web is rotated while a portion of the web which is to be the outer surface is in contact with the configuration-forming receptacle.

Both of these machines have the advantage of rapidly forming a tampon from a web of absorbent material, the web being easily produced on conventional machinery. The tampon produced from both machines, however, suffers from the same disadvantage. After the tampon is used and withdrawal is desired the pledget tends to unwind. This unwinding, due to the exertion of withdrawal force on the string, produces an elongated twisted unsightly tampon which is messy to handle and difficult to withdraw. Attempts at minimizing the telescoping problem have included utilizing adhesive in localized areas so that during the winding and compressive setting of the tampon the adhesive will be activated. This step is complicated, and also could interfere with tampon absorbency.

It is also known that integrity of conventional absorbent cellulosic material which is used in a tampon of this construction, typically, can be increased by local compression i.e. by embossing or contacting with needles. While this step has been attempted on the wound tampons during the winding process per se, its success has been limited.

SUMMARY OF THE INVENTION

According to the process of this invention the telescoping problem can be substantially eliminated by winding the tampon in the presence of a tapering collar. The tampon resulting is of a truncated conical shape. The withdrawal string is located at the base of the truncated cone. The base, by the nature of the winding is subject to a higher degree of compression than the remainder of the tampon. The shape plus the increased compression substantially eliminates the telescoping problem.

DESCRIPTION OF THE DRAWINGS

The application can be more easily understood by reference to the drawings in which.

Figure 1:
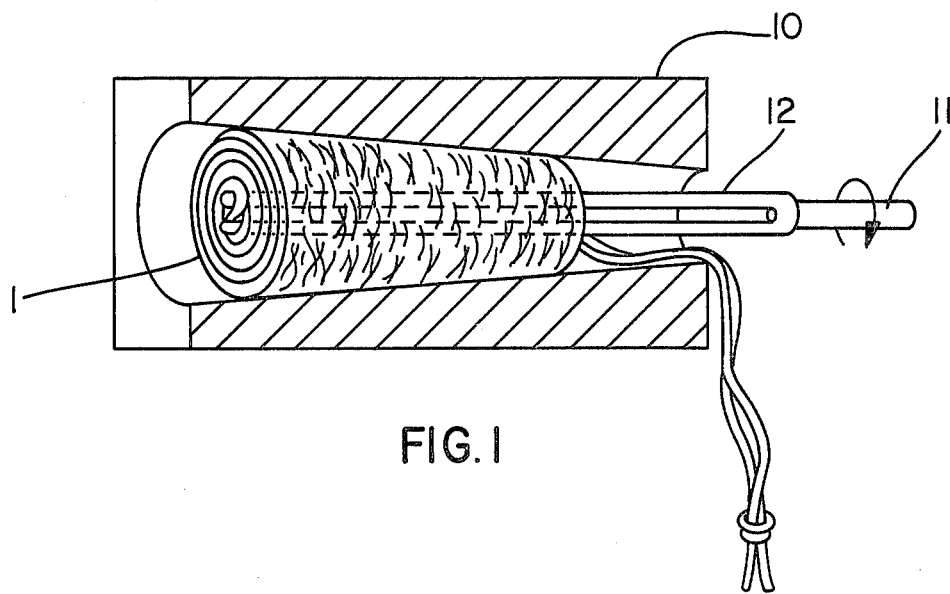
FIGS. 1 and 2 are diagrammatic representations of the winding step according to the teachings of this invention.

According to FIG. 1 the tampon is wound by the winding fork 11 by insertion of the tampon about the tines 12. Rotation of the tampon 1 by the winding fork 11 while in contact with tapering collar 10 provides the conical shape which is the basis for the process of this invention.

Figure 2:
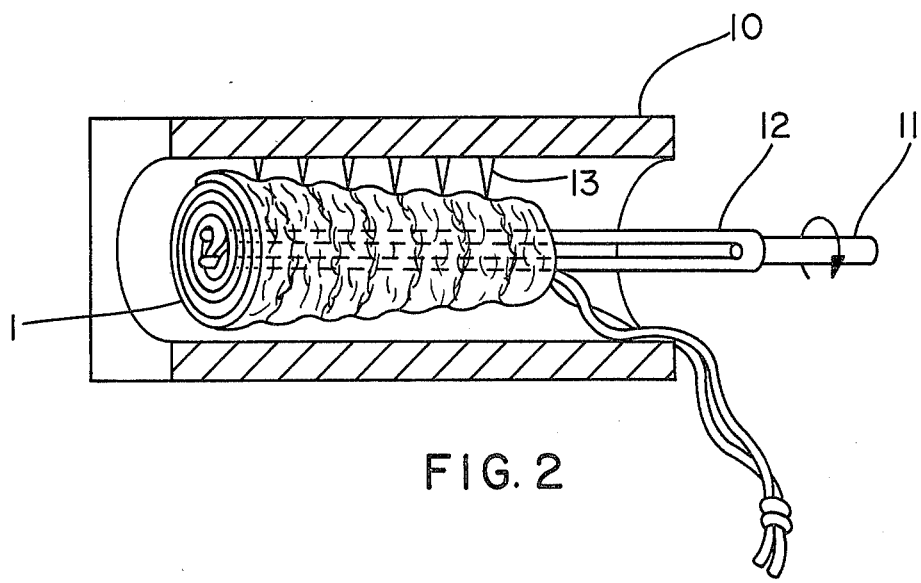

An alternative embodiment is shown in FIG. 2 in which needles 13 of increasing length are provided to form a portion of the collar 10 to shape the tampon. This spot compression achieved by the tapering needles tends to add further integrity. The tampon produced according to FIG. 2 is somewhat of a bell shaped configuration in which raised and depressed areas are noted along the external surface rather than a smooth taper. For purposes of this invention, however, the truncated conical shape described is meant to encompass both embodiments.

It is apparent that further alternatives are possible including a set of opposed needles 13 located on the bottom of the collar 10 which could be offset or opposing the needles depicted in FIG. 2. It is also possible to utilize a tapering collar with needles of the same length. In any event, the tampon made according to the process of this invention retains its integrity during withdrawal and it appears to provide a much better sealing action due to the outwardly tapering conical configuration.

Also, the particular configuration apparently resists early leakage because it blocks by-pass flow.

The shape also promotes easy removal due to the smaller diameter leading end.

What is claimed is:

1. A method for making a tampon having a rolled pledget in the shape of a truncated cone, said method comprising winding a rectangular sheet of absorbent material to form a rolled pledget while the outer surface of the roll is in contact with a tapering receptacle with the narrower portion of the opening in the collar corresponding to the part of the pledget which has the narrowest diameter.

2. The method of claim 1 in which the tapering receptacle is formed by a plurality of needles.

3. The method of claims 1 or 2 in which at least one of the needles is of different length than other of said needles with the longest designed to engage the pledget portion with the smallest diameter.

4. A tampon comprising a rolled pledget in the form of a bell shape with raised and depressed areas along the surface, said tampon having a withdrawal string positioned at the head of the bell.

* * * * *